United States Patent
Maloley et al.

(10) Patent No.: US 11,794,221 B2
(45) Date of Patent: Oct. 24, 2023

(54) SYSTEMS AND METHODS FOR SANITIZING COMPUTING DEVICES

(71) Applicant: Vivacity Tech PBC, Dover, DE (US)

(72) Inventors: Eli Maloley, Saint Paul, MN (US); Samar Elmaghraby, Cairo (EG); Timothy Orton, Royalton, MN (US)

(73) Assignee: VIVACITY TECH PBC, Dover, DE (US)

( * ) Notice: Subject to any disclaimer, the term of this patent is extended or adjusted under 35 U.S.C. 154(b) by 507 days.

(21) Appl. No.: 16/941,268

(22) Filed: Jul. 28, 2020

(65) Prior Publication Data

US 2022/0032345 A1 Feb. 3, 2022

(51) Int. Cl.
*B08B 7/00* (2006.01)
*A61L 2/10* (2006.01)
*B62B 3/00* (2006.01)

(52) U.S. Cl.
CPC ............ *B08B 7/0057* (2013.01); *A61L 2/10* (2013.01); *B62B 3/005* (2013.01); *A61L 2202/20* (2013.01); *B62B 2202/56* (2013.01)

(58) Field of Classification Search
CPC .......... A61L 2202/20; A61L 2202/122; A61L 2202/16; B62B 2202/56
See application file for complete search history.

(56) References Cited

U.S. PATENT DOCUMENTS

| | | |
|---|---|---|
| 8,481,970 B2 | 7/2013 | Cooper et al. |
| 8,752,848 B2 | 6/2014 | Petrick et al. |
| 9,330,520 B2 | 5/2016 | Phelps et al. |
| 9,492,576 B1 | 11/2016 | Cudak et al. |
| 10,084,327 B2 | 9/2018 | Roberts |
| 10,166,308 B2 | 1/2019 | Engelhardt et al. |
| 10,272,167 B2 | 4/2019 | Starkweather et al. |
| 10,396,574 B2 | 8/2019 | Maguire et al. |
| 10,439,408 B1 | 10/2019 | Bastiyali |
| 2014/0264075 A1* | 9/2014 | LaPorte ............... A61L 2/00 250/455.11 |
| 2016/0000953 A1 | 1/2016 | Bettles et al. |

(Continued)

FOREIGN PATENT DOCUMENTS

CN 106943609 A 7/2017

OTHER PUBLICATIONS

AVerCharge X18iS, "18 Device Intelligent Charging Cart with UV Sanitization", Averusa datasheet, 2021.

(Continued)

*Primary Examiner* — Natasha N Campbell
(74) *Attorney, Agent, or Firm* — Fox Rothschild LLP; Carol Thorstad-Forsyth

(57) ABSTRACT

Systems and methods for operating a cart. The methods comprise: receiving an electronic device on a shelf disposed in a main chamber of the cart; supplying power from the cart to the electronic device; transitioning a mode of the cart from a first mode in which a UV lamp is disabled to a second mode during which the UV lamp is to be enabled; detecting, by a computing device, that a door of the cart is in a closed position; causing, by the computing device, an enablement of the UV lamp, responsive to a detection that the door is in the closed position; and using light from the UV lamp to clean the surface of the electronic device while power is being supplied from the cart to the electronic device.

9 Claims, 14 Drawing Sheets

(56) References Cited

U.S. PATENT DOCUMENTS

| | | |
|---|---|---|
| 2016/0072325 A1 | 3/2016 | Su et al. |
| 2016/0158395 A1 | 6/2016 | Hughes et al. |
| 2016/0228591 A1 | 8/2016 | Engelhardt et al. |
| 2017/0119151 A1* | 5/2017 | Barber ................. A47B 43/003 |
| 2017/0296686 A1 | 10/2017 | Cole |
| 2019/0047460 A1 | 2/2019 | Goldberg et al. |
| 2019/0165585 A1 | 5/2019 | Grison |

OTHER PUBLICATIONS

International Search Report and Written Opinion issued in PCT/US2021/042393 dated Oct. 20, 2021.

Stewart Balanchine, ChargeMax T & C "Disinfecting Charging Carts for Schools: Total Quality care, Health & Safety" (retrieved from https://www.cetrixtablets.com/wp-content/uploads/2017/07/ChargeMax-T-and-Cver-1.5.pdf on May 8, 2020).

* cited by examiner

Go to FIG. 19B

SYSTEMS AND METHODS FOR SANITIZING COMPUTING DEVICES

BACKGROUND

The present disclosure relates generally to sanitizing devices. More particularly, the present disclosure relates to implementing systems and methods for sanitizing computing devices.

SUMMARY

The present disclosure concerns implementing systems and methods for operating a cart. The methods comprise receiving at least one electronic device (e.g., in an open position) on a shelf of a plurality of shelves disposed in a main chamber of the cart. The shelf is configured to allow UV light to pass therethrough to a surface of the electronic device. In this regard, the shelf may comprise a wire shelf or a shelf formed of a transparent material. The methods also comprise: supplying power from the cart to the electronic device; transitioning a mode of the cart from a first mode (e.g., a standby mode) in which at least one UV lamp is disabled to a second mode (e.g., a quick clean mode or a deep clean mode) during which at least one UV lamp is to be enabled; detecting, by a computing device, that at least one door of the cart is in a closed position; causing, by the computing device, an enablement of the at least one UV lamp that is disposed in the main chamber of the cart, responsive to a detection that the at least one door is in the closed position; and using light from the at least one UV lamp to clean the surface of the electronic device while power is being supplied from the cart to the electronic device.

In some scenarios, the methods also comprise: detachably coupling at least one cable to the shelf (where the cable facilitates a supply of power from the cart to the electronic device); and/or detachably coupling the at least one door to the shelf when the at least one door is in the closed position. Additionally or alternatively, the methods comprise: detecting that the at least one door is being opened while the surface of the electronic device is being cleaned via the UV lamp(s); disabling the UV lamp(s) responsive to a detection that the door(s) is(are) being opened; detecting when the door(s) is(are) once again in the closed position; enabling the UV lamp(s) responsive to a detection that that the door(s) is(arE) once again in the closed position; and/or disabling the UV lamp(s) upon expiration of a given period of time. The mode of the cart can be transitioned from the second mode back to the first mode upon completion of a cleaning process in which the UV lamp(s) is(are) used to clean the surface of the electronic device.

In those or other scenarios, the methods comprise: detecting when an individual is in proximity to the cart; detecting behavior of the individual using a machine learning algorithm; and disabling the UV lamp(S) when the behavior is of a given type.

The present document also concerns carts. Each cart comprises: a housing with on or more doors; a plurality of shelves disposed in a main chamber provided within the housing (where each of the shelves (i) is sized and shaped to receive at least one electronic device, for example, in an open position and (ii) is configured to allow UV light to pass therethrough to a surface of the electronic device); a power supply component configured to supply power from the cart to the electronic device when the electronic device is disposed in the main chamber of the cart; at least one UV lamp disposed in the main chamber and configured to emit the UV light; a computing device connected to the power supply component and the UV light system. The computing device comprises a processor and a non-transitory computer-readable storage medium comprising programming instructions that are configured to cause the processor to implement a method for operating the cart. The programming instructions comprise instructions to: transition a mode of the cart from a first mode in which the UV lamp(s) is(are) disabled to a second mode during which the UV lamp(s) is(are) to be enabled; detect that the door(s) is(are) in a closed position; and cause an enablement of the UV lamp(s), responsive to a detection that the door(s) is(are) in the closed position. The UV light from the UV lamp(s) clean(s) the surface of the electronic device while power is being supplied from the power supply component to the electronic device.

The cart may also comprise: a coupler configured to detachably couple at least one cable to a shelf of the cart, the cable facilitating a supply of power from the power supply component to the electronic device; and/or a coupler configured to detachably couple a door to a shelf when the door is in the closed position.

The programming instructions may also comprise instructions to: detect that the door(s) is(are) being opened while the surface of the electronic device is being cleaned via the UV lamp(s); cause a disablement of the UV lamp(s) responsive to a detection that the door(s) is(are) being opened; detect when the door(s) is(are) once again in the closed position; cause an enablement of the UV lamp(s) responsive to a detection that that the door(s) is(are) once again in the closed position; and/or transition the mode of the cart from the second mode back to the first mode upon a disablement of the UV lamp(s) in response to an expiration of a given period of time and/or upon a completion of a cleaning process.

The programming instructions may further comprise instructions to: detect when an individual is in proximity to the cart; detect behavior of the individual using a machine learning algorithm; and cause a disablement of the UV lamp(s) when the behavior is of a given type.

BRIEF DESCRIPTION OF THE DRAWINGS

The present solution will be described with reference to the following drawing figures, in which like numerals represent like items throughout the figures.

DETAILED DESCRIPTION

Figure 1:
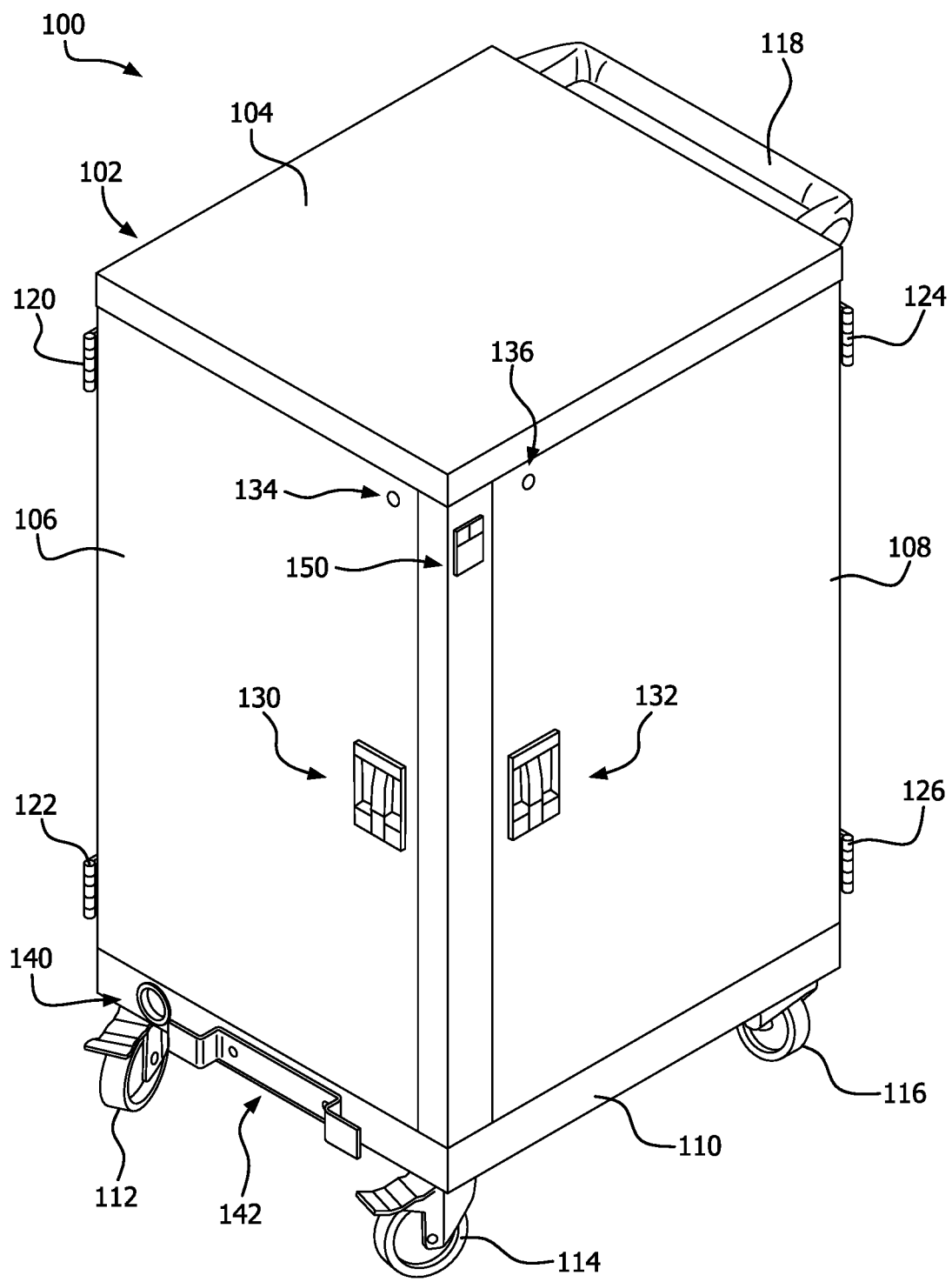
FIG. 1 provides a front perspective view of an illustrative cart with closed doors.

The present solution is described with reference to the attached figures. The figures are not drawn to scale and they are provided merely to illustrate the instant solution. Several aspects of the present solution are described below with reference to example applications for illustration. It should be understood that numerous specific details, relationships, and methods are set forth to provide a full understanding of the present solution. One having ordinary skill in the relevant art, however, will readily recognize that the present solution can be practiced without one or more of the specific details or with other methods. In other instances, well-known structures or operations are not shown in detail to avoid obscuring the present solution. The present solution is not limited by the illustrated ordering of acts or events, as some acts may occur in different orders and/or concurrently with other acts or events. Furthermore, not all illustrated acts or events are required to implement a methodology in accordance with the present solution.

It should also be appreciated that the terminology used herein is for the purpose of describing particular embodiments only and is not intended to be limiting of the present solution. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

An "electronic device" or a "computing device" refers to a device that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions.

The terms "memory," "memory device," "data store," "data storage facility" and the like each refer to a non-transitory device on which computer-readable data, programming instructions or both are stored. Except where specifically stated otherwise, the terms "memory," "memory device," "data store," "data storage facility" and the like are intended to include single device embodiments, embodiments in which multiple memory devices together or collectively store a set of data or instructions, as well as individual sectors within such devices.

The terms "processor" and "processing device" refer to a hardware component of an electronic device that is configured to execute programming instructions. Except where specifically stated otherwise, the singular term "processor" or "processing device" is intended to include both single-processing device embodiments and embodiments in which multiple processing devices together or collectively perform a process.

In this document, when terms such as "first" and "second" are used to modify a noun, such use is simply intended to distinguish one item from another, and is not intended to require a sequential order unless specifically stated. In addition, terms of relative position such as "vertical" and "horizontal", or "front" and "rear", when used, are intended to be relative to each other and need not be absolute, and only refer to one possible position of the device associated with those terms depending on the device's orientation.

Further, unless otherwise defined, all terms (including technical and scientific terms) used herein have the same meaning as commonly understood by one of ordinary skill in the art to which this solution belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present solution generally relates to a cart for storing and/or sanitizing computing devices. Illustrations of an illustrative cart are provided in FIGS. 1-7. As shown in FIGS. 1-7, the cart 100 comprises a housing 102 having a generally rectangular shape. The present solution is not limited in this regard. The housing 102 can have any shape selected in accordance with a given application. For example, the housing 102 can alternatively have a square shape or a circular shape. The housing 102 comprises a top panel 104, a bottom panel 110, side panels 200, 202, and two doors 106, 108. The panels and doors may be formed of metal, plastic and/or any other material suitable for a given application. The top, bottom and side panels 104, 110, 200, 204 are securely coupled to each other via weld(s), adhesive(s) and/or mechanical coupler(s) (e.g., screws, bolts, nuts, latches, clamps, etc.). The top, bottom and side panels 104, 110, 200, 204 have fixed positions relative to each other when coupled together.

A handle 118 is securely coupled to the side panel 202. Casters 114-116 are securely coupled to the bottom panel 110. The handle 118 and casters 114-116 facilitate relocation and/or movement of the cart 100 by an individual. The handle 118 can be formed of metal, plastic, rubber and/or any other material selected in accordance with a given application. The handle 118 can have an ergonomic design to provide a comfortable gripping surface. An antimicrobial film may be disposed on the handle 118 for preventing or inhibiting growth and reproduction of bacteria, molds, mildew and fungi. Any known to be known antimicrobial film and/or casters can be used here without limitation. In some scenarios, the casters are able to swivel, and/or have rubber wheels and/or locks.

Door 106 is rotatably coupled to the side panel 200 so that the door can be opened and closed by an individual. Similarly, door 108 is rotatably coupled to side panel 202 so that the door can be opened and closed by an individual. The doors 106, 108 are shown in their fully closed positions in FIG. 1, and their fully opened positions in FIG. 2. The rotatable coupling of the doors 106, 108 is facilitated by a plurality of hinges 120, 122, 124, 126. The hinges 120-126 are respectively coupled to the doors 106, 108 and side panels 200, 202 via welds(s), adhesive(s) and/or mechanical couplers (e.g., screws). The hinges 120-126 are configured so that the doors 106, 108 have an angle of rotation equal to 270° relative to the side panels 200, 202, respectively. The hinges 120-126 are the same as or substantially similar to each other.

Figure 13:
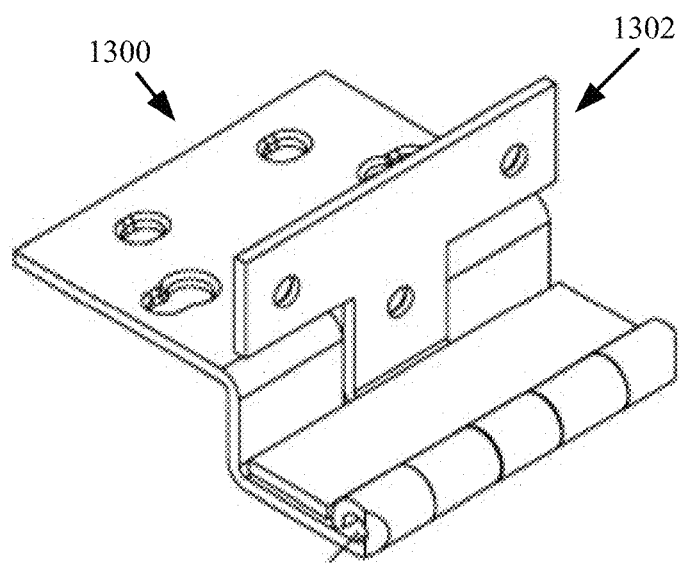
FIGS. 13-14 each provide a perspective view a hinge of the cart of FIG. 1.
Figure 14:
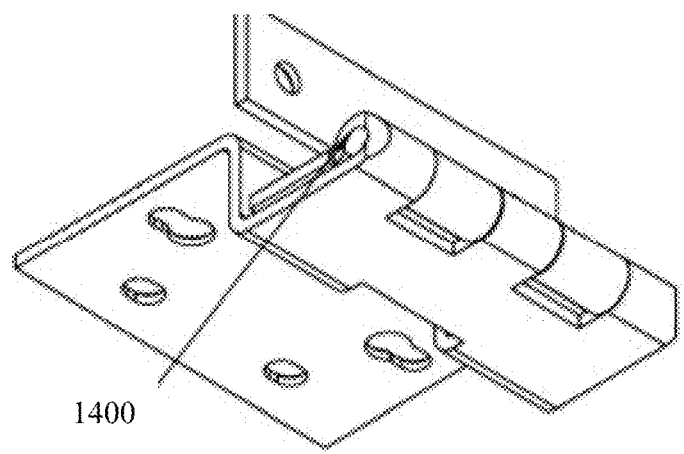
Figure 15:
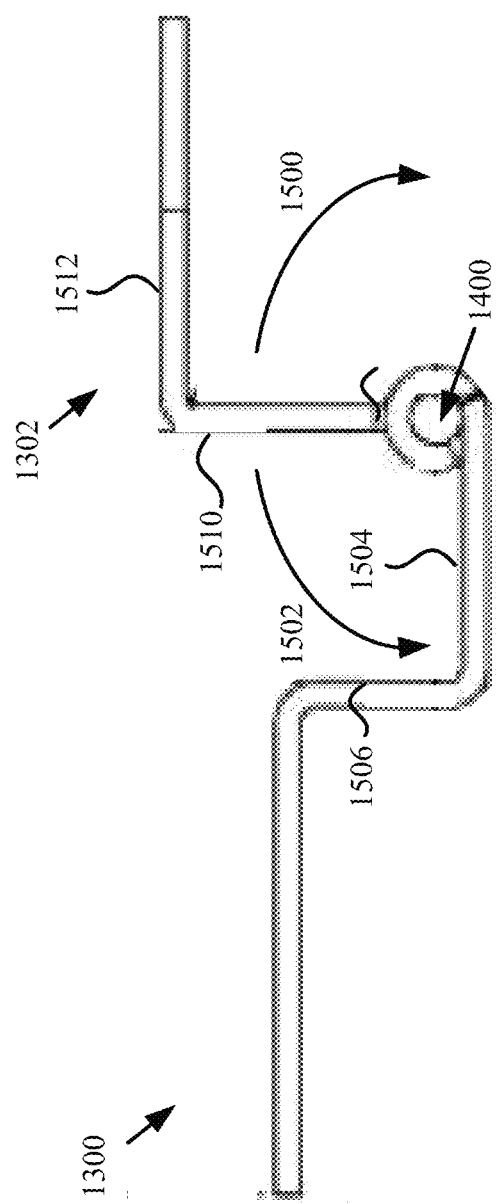
FIG. 15 provides a side view of the hinge shown in FIGS. 13-14.

An illustrative architecture for the hinges 120-126 is provided in FIGS. 13-15. In FIGS. 13-15, the hinge is generally designed to enable a door to pivot on one edge as it opens and closes. In this regard, the hinge comprises two parts 1300, 1302 that are joined by a pin 1400 about which the parts 1300, 1302 are able to turn. A first part 1300 is coupled to the side panel 200 or 202, while the second part 1302 is coupled to the door 106 or 108. The first part 1300 maintains its position relative to the cart's housing 102 while in use, while the second part 1302 has a variable position relative to the cart's housing 102 while in use. The position of the second part 1302 is changed via the opening and closing of the door 106 or 108. The first and second parts are designed to allow the door to be able to rotate 270° relative to the cart's housing 102. In this regard, the first part 1300 has a generally Z-shape, and the second part 1302 has a generally L-shape. When the hinge is coupled between a side panel and door, the second part 1302 is able to rotate in two opposing directions shown by arrows 1500, 1502 of FIG. 15. The second part 1302 rotates in direction 1500 away from the first part 1300 when the door is being opened, and rotates in direction 1502 towards the first part 1300 when the door is being closed. When the door is fully closed, the second part 1302 abuts the first part 1300 whereby (i) surface 1510 of the second part 1302 contacts surface 1504 of the first part 1300, and (ii) surface 1512 of the second part 1302 contacts surface 1506 of the first part 1300.

Each door 106, 108 has a door latch 130, 132. The door latch 130, 132 comprises a spring-loaded lock that can be opened from the outside by an individual. The door latch 130, 132 is provided to keep the door firmly closed. Any known or to be known door latch can be used here. An antimicrobial film may be disposed on each door latch 130, 132 for preventing or inhibiting growth and reproduction of bacteria, molds, mildew and fungi. Any known to be known antimicrobial film can be used here without limitation.

Figure 16:
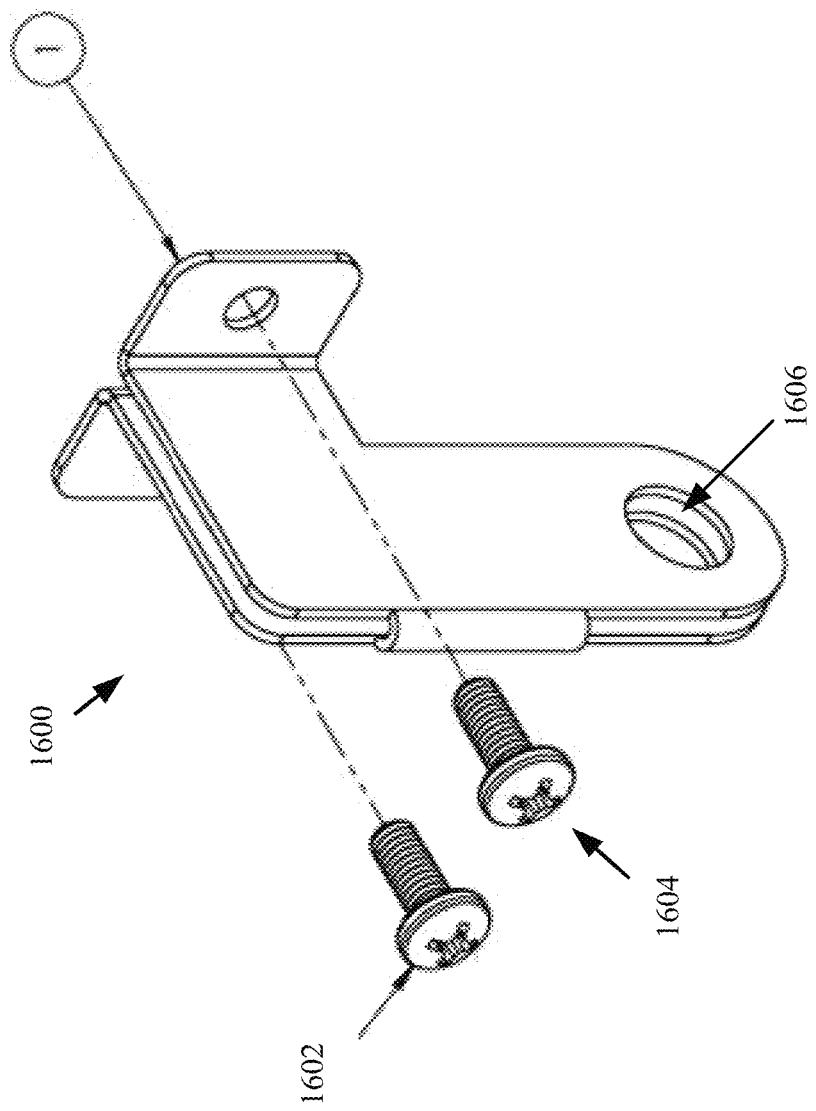
FIG. 16 provides a perspective view of an illustrative padlock coupling structure for the cart of FIG. 1.

A padlock coupling structure 134, 136 may also be provided with the cart 100 for each door 106, 108. An illustration of an illustrative padlock coupling structure is provided in FIG. 16. The padlock coupling structure is securely coupled to the cart's housing 102 via weld(s), adhesive(s) and/or mechanical couplers (e.g., screws 1602, 1604 of FIG. 16). The padlock coupling structure 1600 is positioned on the housing such that it is aligned with and at least partially passes through an aperture formed in a door, when the door is in its closed position shown in FIG. 1. The padlock coupling structure comprises an aperture 1606 formed therein that is sized and shaped to removably receive a shackle of a padlock (not shown in FIGS. 1-16).

A power cord is also provided with the cart 100. The power cord is not shown in FIGS. 1-12 simply for ease of illustration. The power cord is provided to couple the electronic components of the cart 100 to a power source (e.g., an AC mains and/or a conventional wall outlet). The power cord passes through aperture(s) 140, 240 formed in the cart housing 102. The power cord may be configured to be withdrawn out of the housing 102 and retracted into the housing 102. A power cord holder 142 may be provided for storing the power cord when not in use. The power cord holder 142 is designed so that the power cord can be wrapped there around without coming undone.

A touch screen display 150 is also disposed on the cart 100. The touch screen display 150 may include, but is not limited to, a Liquid Crystal Display ("LCD"). The touch screen display 150 is configured to allow an individual to perform user-software interactions for (i) selecting a cleaning mode from a plurality of cleaning modes, (ii) start a cleaning process for sanitizing electronic devices disposed inside the cart 100, and/or (iii) terminate a cleaning process. The particulars of the cleaning process will become evident as the discussion progresses. The cleaning modes can include, but are not limited to, a quick clean mode in which a relatively short cleaning process is performed (e.g., a 5 minutes cleaning process), and/or a deep clean mode in which a relatively long cleaning process is performed (e.g., a 240 minute cleaning process). An antimicrobial film may be disposed on the touch screen display 150 for preventing or inhibiting growth and reproduction of bacteria, molds, mildew and fungi. Any known to be known antimicrobial film can be used here without limitation.

Figure 2:
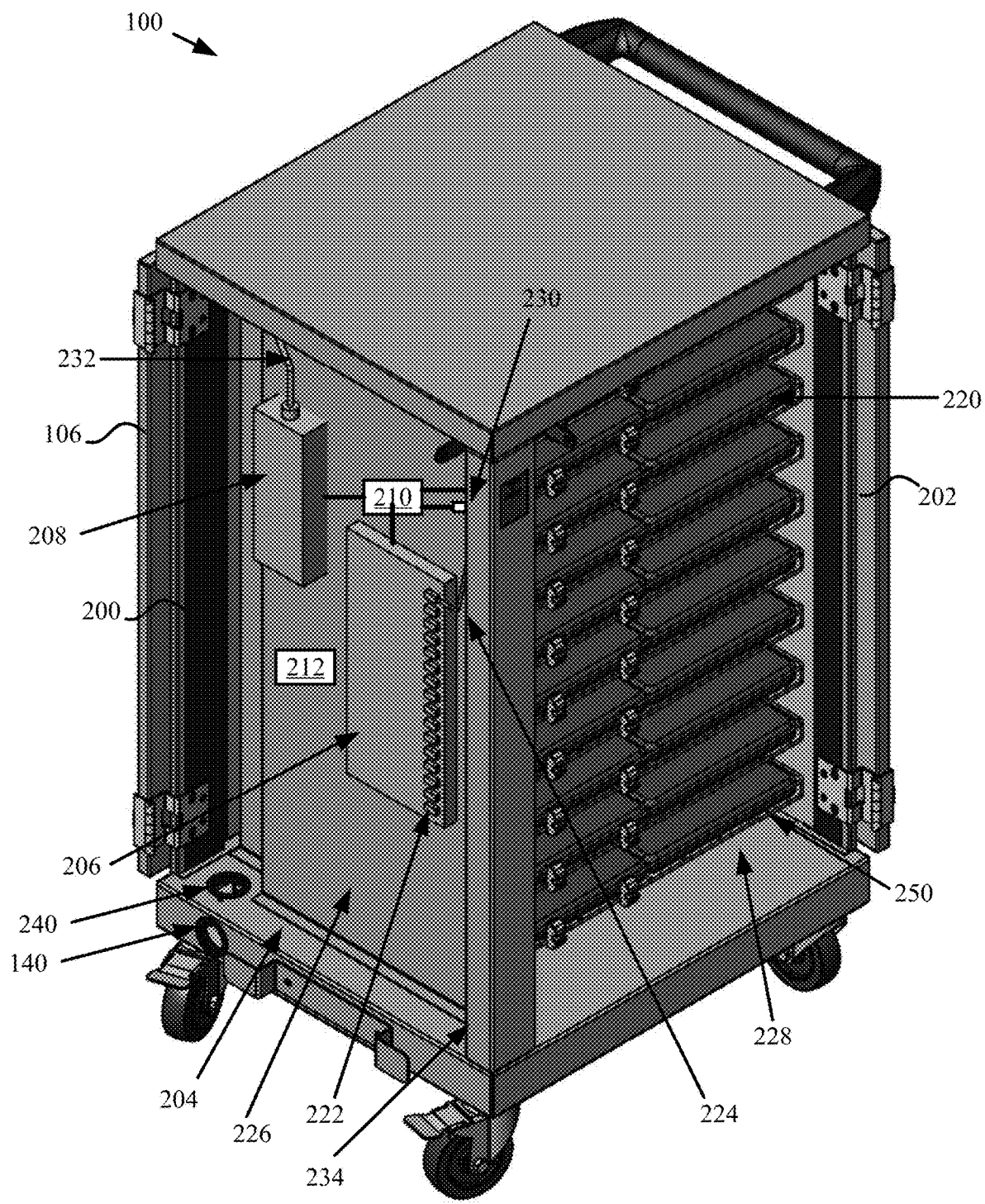
FIG. 2 provides a front perspective view of the cart shown in FIG. 1 with open doors.
Figure 3:
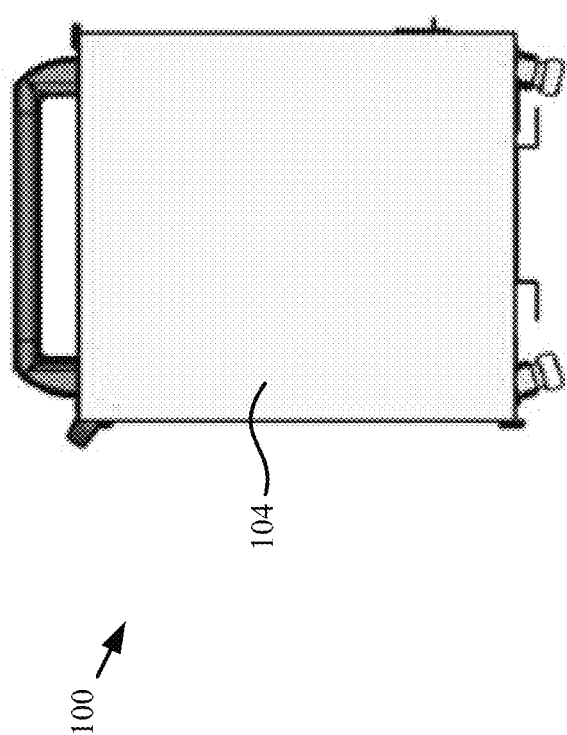
FIG. 3 provides a top view of the cart shown in FIG. 1.
Figure 4:
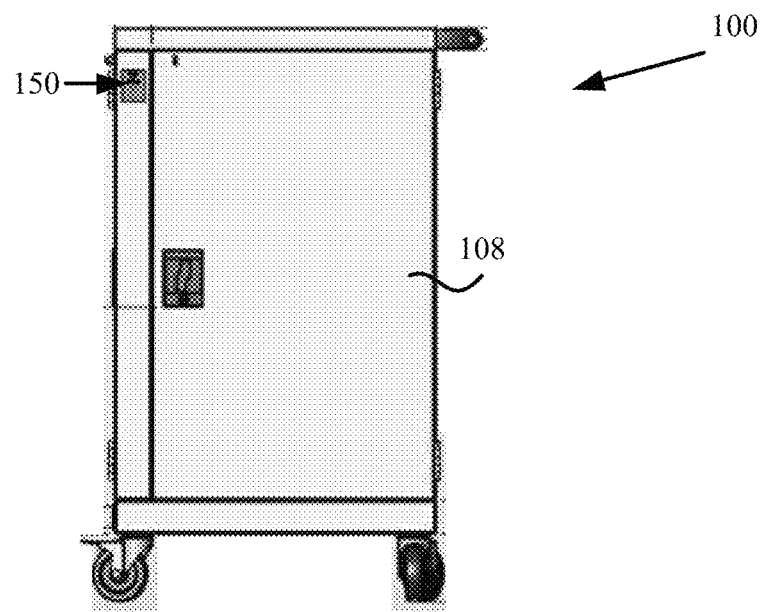
FIG. 4 provides a front view of the cart shown in FIG. 1 with a closed door.

As shown in FIG. 2, various electronic components are disposed in an internal space 204 of the cart 100. An individual can access the internal space 204 via door 106. The electronic components include, but are not limited to, a power supply component 206, a UV lamp ballast component 208, a computing device 210, and sensor(s) 230. All of the listed components 206, 208, 210, 230 may be supplied power from an external power source via the power cord (not shown in FIG. 2). A local power source 212 may additionally or alternatively be provided with the cart 100 to power components 206, 208, 210, 230. The local power source can include, but is not limited to, a rechargeable battery and/or an energy harvesting circuit. Batteries and energy harvesting circuits are well known. The energy harvesting circuit may harvest energy from light, RF signals, vibration, heat and/or magnetic fields.

The power supply component 206 is mounted on the divider wall 226 of the cart 100 via weld(s), adhesive(s) and/or mechanical couplers (e.g., screws). The power supply component 206 is configured to allow power to be selectively supplied from a power source (e.g., the external power source and/or the battery 212) to electronic devices 220 disposed in a main chamber 228 of the cart 100 (e.g., for charging and/or recharging internal power sources of the electronic devices). The electronic devices 220 can include, but are not limited to, smart phones, laptop computers, tablet computers, personal digital assistants, smart watches, smart goggles, and/or smart glasses. In some scenarios, the power supply component 206 comprises a plurality of USB and/or USB-C ports 222 to facilitate an electrical connection between the power supply component 206 and the electronic devices 220. The total number of ports 222 is selected in accordance with a given application. For example, if the cart 100 is designed to receive a maximum of 10 electronic devices in the main chamber 228, then 10 ports 222 are provided. The present solution is not limited to the particulars of this example. Pre-installed cables 224 are provided with the cart 100 to facilitate the electronic connections between the ports 222 and the electronic devices 220.

Figure 7:
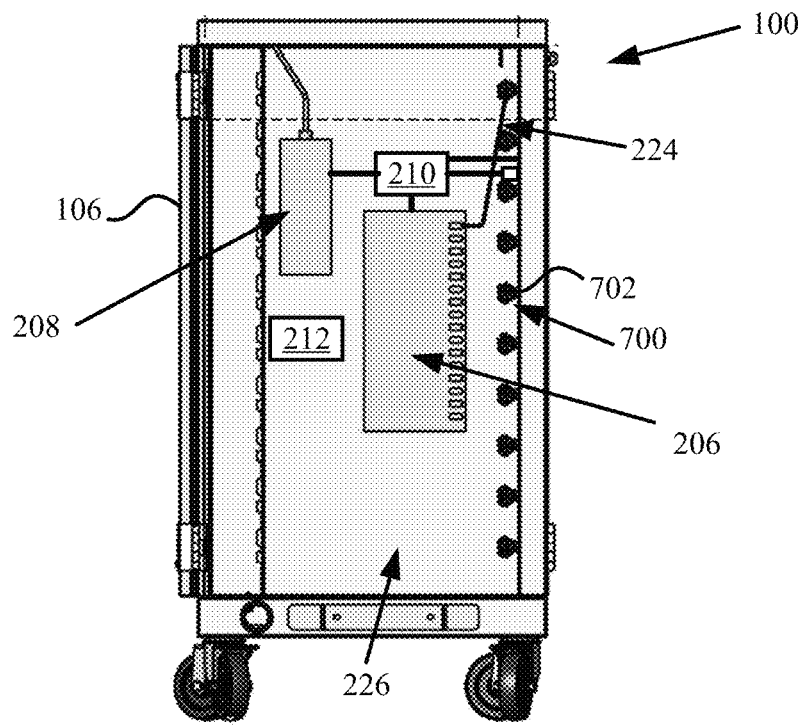
FIG. 7 provides a side view of the cart shown in FIG. 1 with an open door.
Figure 9:
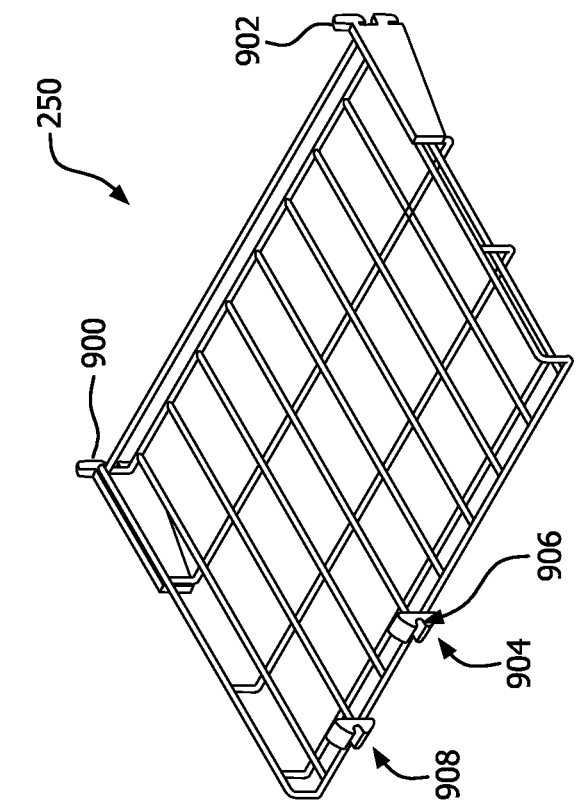
FIG. 9 provides a perspective view of the shelf shown in FIG. 8.
Figure 8:
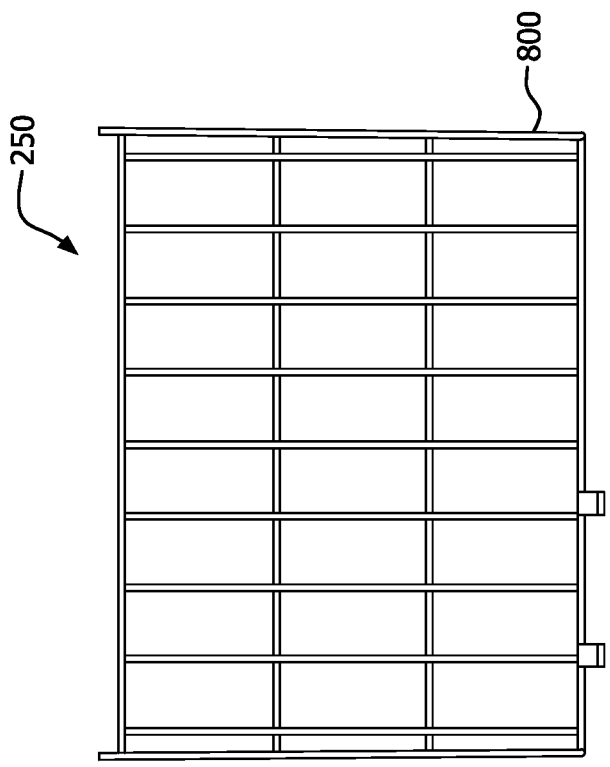
FIG. 8 provides a top view of an illustrative shelf.
Figure 11:
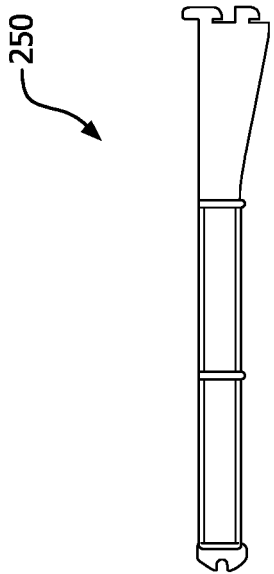
FIG. 11 provides a side view of the shelf shown in FIG. 8.
Figure 10:
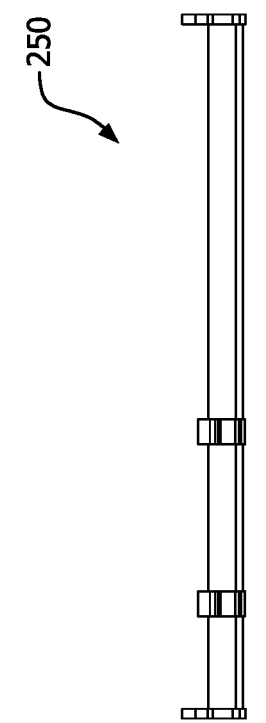
FIG. 10 provides a front view of the shelf shown in FIG. 8.

Each cable 224 passes through an aperture 700 formed in a divider wall 226 of the cart 100, as shown in FIG. 7. A grommet 702 may be disposed in each aperture 700. In this scenario, each cable 224 may also pass through the grommet 702. The grommet 702 provides a means to control an amount of cable 224 that is pulled into the main chamber 228 of the cart 100. This ensures that the cable 224 does not become disconnected from the power supply component 206 when being coupled to an electronic device 220 disposed in the main chamber 228 of the cart 100. Additionally or alternatively, a mechanism (not shown) (e.g., a spool, gears and/or a motor) can be provided for allowing each cable 224 to be withdrawn from the internal space 204 of the cart 100, and retracted into the internal space 204 of the cart 100.

The UV lamp ballast component 208 is mounted on the divider wall 226 of the cart 100 via weld(s), adhesive(s) and/or mechanical couplers (e.g., screws). The UV lamp ballast component 208 comprises wire(s) 232 connected in series with at least one UV lamp 500 disposed in the main chamber 228 of the cart 100. The UV lamp ballast component 208 is configured to perform two functions: (i) initially provide a high voltage charge to ionize mercury in the UV lamp(s) 500; and (ii) reduce the voltage and amperage required to keep the mercury ionized throughout a cleaning process. In some scenarios, the UV lamp ballast component 208 comprises a UV lamp ballast having a part number PH9-2100-320 which is available from Renownuv Electric Co., Ltd. of China. The UV lamp ballast component 208 and UV lamp(s) 500 are collectively referred to herein as a UV lamp system.

The UV lamp(s) 500 is configured to facilitate the sanitization and disinfection of the electronic devices 220 while they are being stored in the cart 100 and/or being charged by the power supply component 206. The UV lamp(s) 500 use(s) short-wavelength ultraviolet ("UV-C") light to kill or inactivate microorganisms on the surfaces of the electronic devices 220. The UV lamp(s) are positioned within the cart 100 such that the sanitization of all electronic devices 220 stored in the cart is successfully accomplished.

Figure 5:
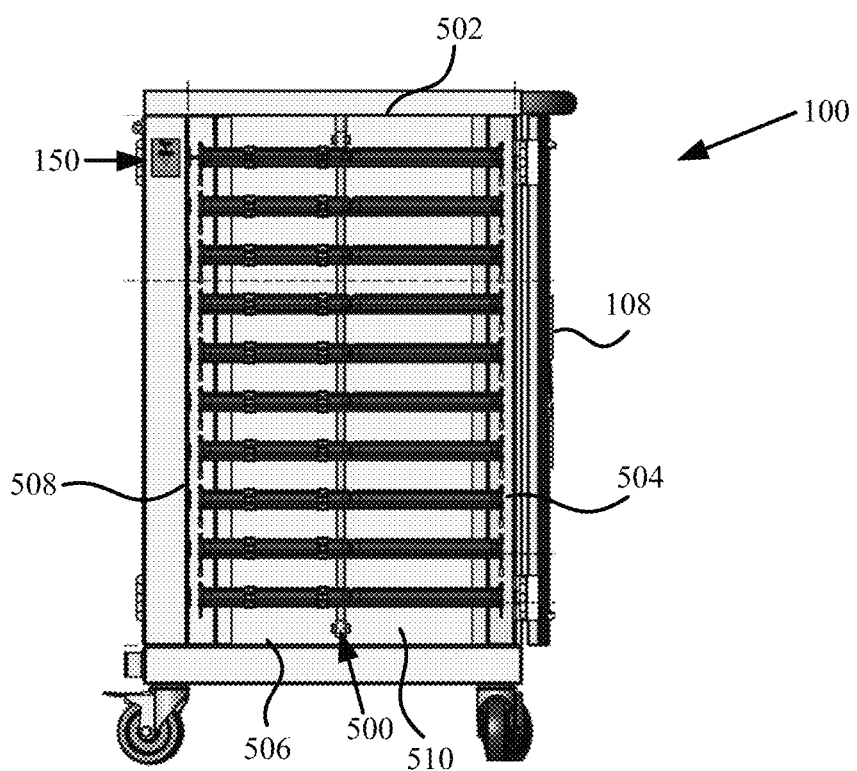
FIG. 5 provides a front view of the cart shown in FIG. 1 with an open door and computing devices disposed therein.
Figure 6:
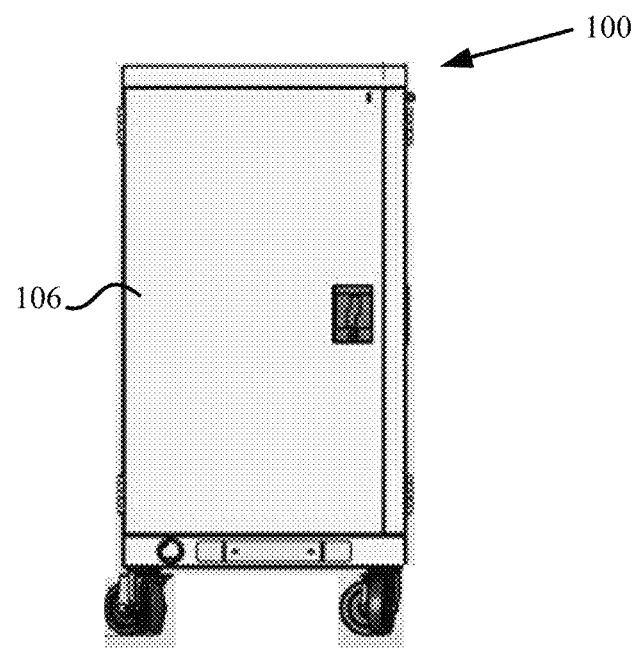
FIG. 6 provides a side view of the cart shown in FIG. 1 with a closed door.
Figure 12:
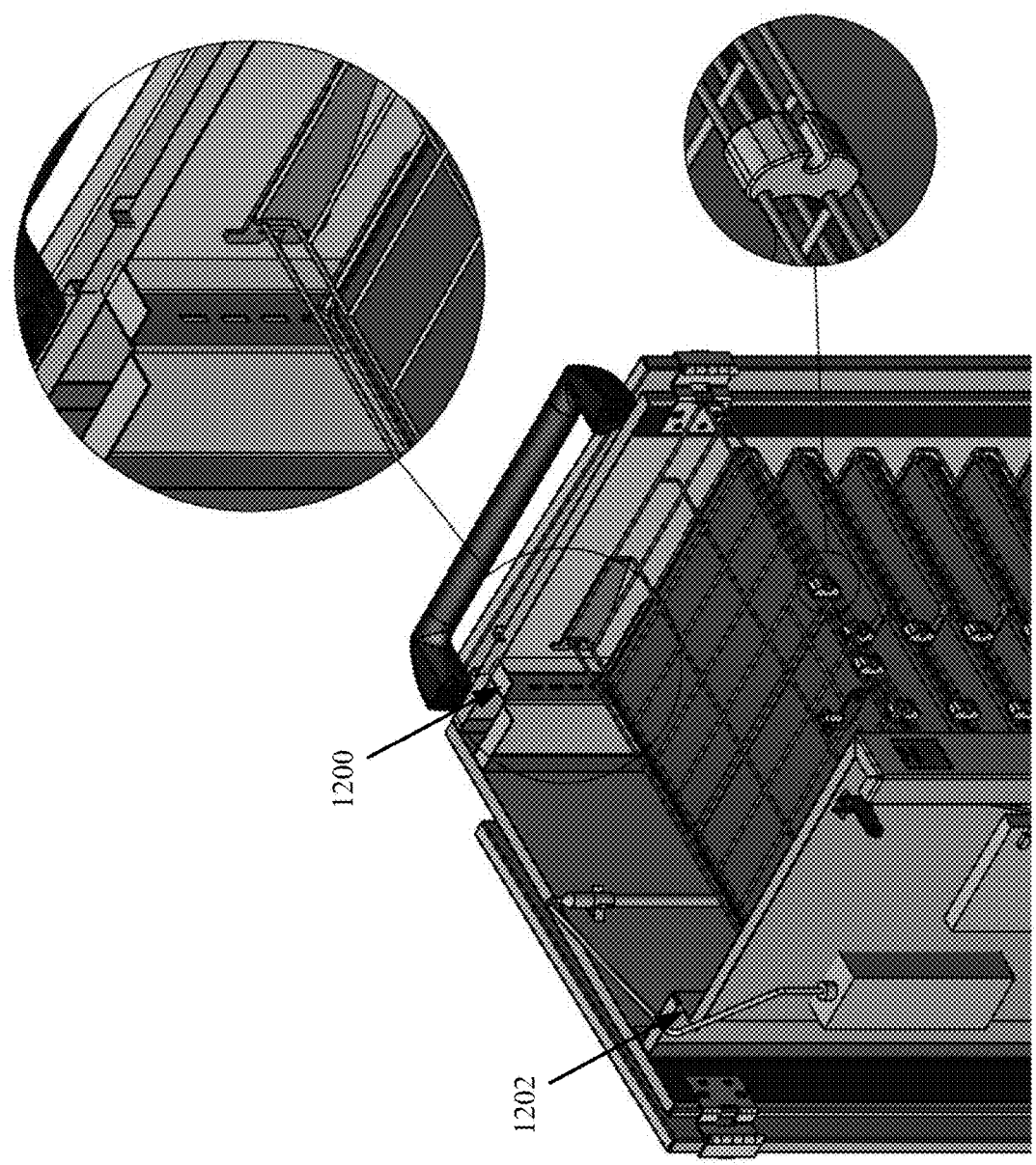
FIG. 12 provides a partial perspective view that is useful for understanding how the shelf of FIGS. 8-11 can be disposed in the cart of FIG. 1.

Although a single UV lamp 500 is shown in FIGS. 1-12, the present solution is not limited in this regard. Any number of UV lamps can be provided in accordance with a given application. The UV lamp(s) 500 are coupled to one or more sidewalls 502, 504, 506, 508, 510 of the main chamber 228 via weld(s), adhesive(s) and/or mechanical couplers (e.g., screws). The sidewalls are formed of, coated with, or lined with a highly reflective material (e.g., polished aluminum) to increase the cleaning efficiency of the UV lamps. UV lamps are well known in the art. Any known or to be known UV lamp can be used here. The UV lamp(s) 500 can include, but are not limited to, linear UV lamps that extend horizontally within the cart as shown in FIGS. 5 and 12, vertically within the cart (not shown), diagonally within the cart (not shown). Alternatively or additionally, the UV lamps comprise non-linear UV lamps that are arranged in a linear pattern and/or non-linear pattern on one or more sidewalls 502, 504, 506, 508, 510 of the main chamber 228. The non-linear pattern can include, but is not limited to, a pattern formed by concentric circles, squares and/or rectangles.

Sensor(s) 230 may be mounted on a side wall 234 of the cart 100 via weld(s), adhesive(s) and/or mechanical couplers (e.g., screws). The sensor(s) 230 can include, but are not limited to, magnetic door sensor(s), temperature sensor(s), humidity sensor(s), light sensor(s), vibration sensor(s), accelerometer sensor(s), proximity sensor(s), and/or RFID tag(s). The magnetic door sensor(s) provide a means to detect when a door 106, 108 is opened and/or closed.

Figure 17:
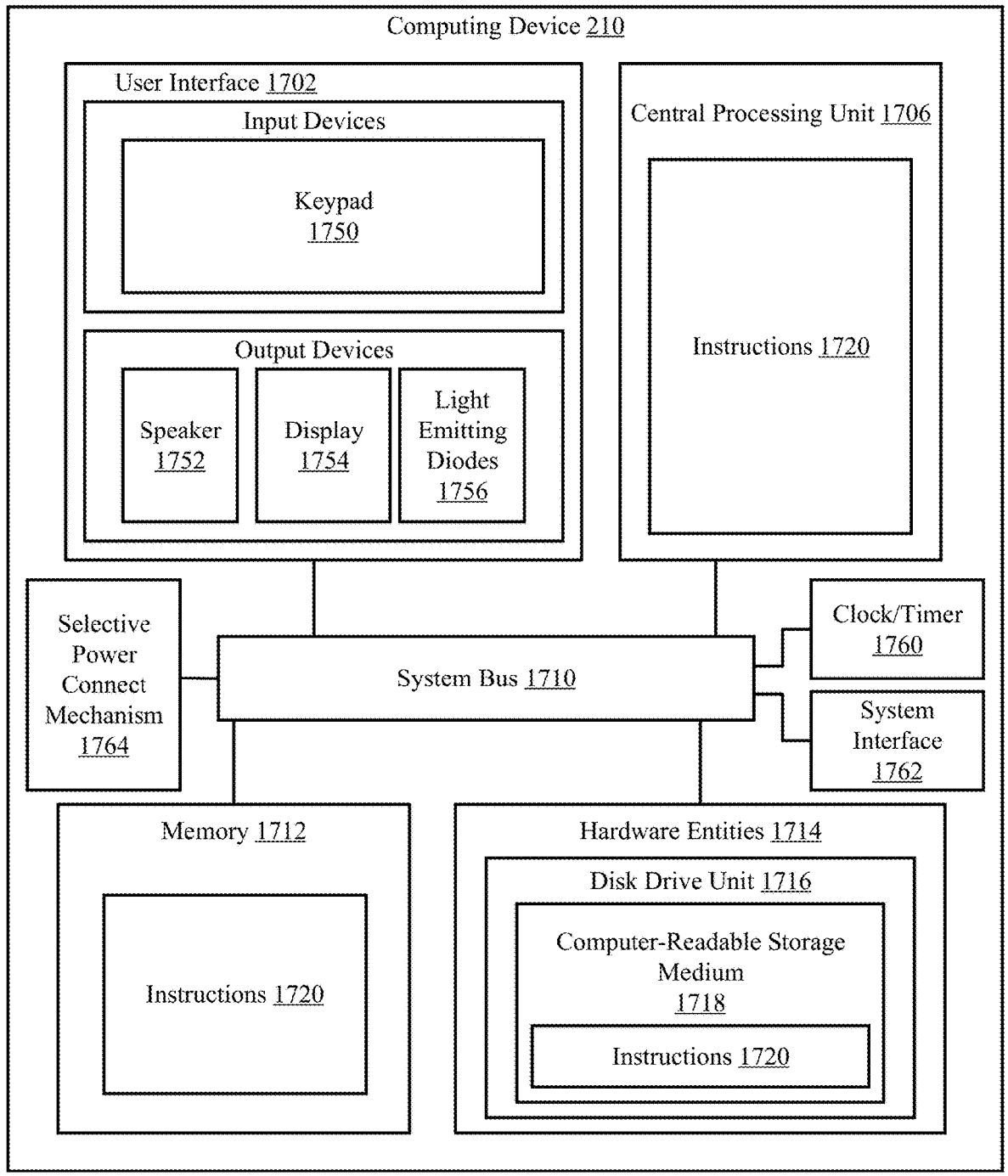
FIG. 17 provides an illustration of an illustrative computing device.

The computing device 210 is mounted on the divider wall 226 of the cart 100 via weld(s), adhesive(s) and/or mechanical couplers (e.g., screws). The computing device 210 is provided to facilitate the control of cart operations. A detailed block diagram of the computing device 210 is provided in FIG. 17. Computing device 210 may include more or less components than those shown in FIG. 17. However, the components shown are sufficient to disclose an illustrative solution implementing the present solution. The hardware architecture of FIG. 17 represents one implementation of a representative computing device configured to operate a cart 100, as described herein. As such, the computing device 210 of FIG. 17 implements at least a portion of the method(s) described herein.

Some or all components of the computing device 210 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

Figure 18:
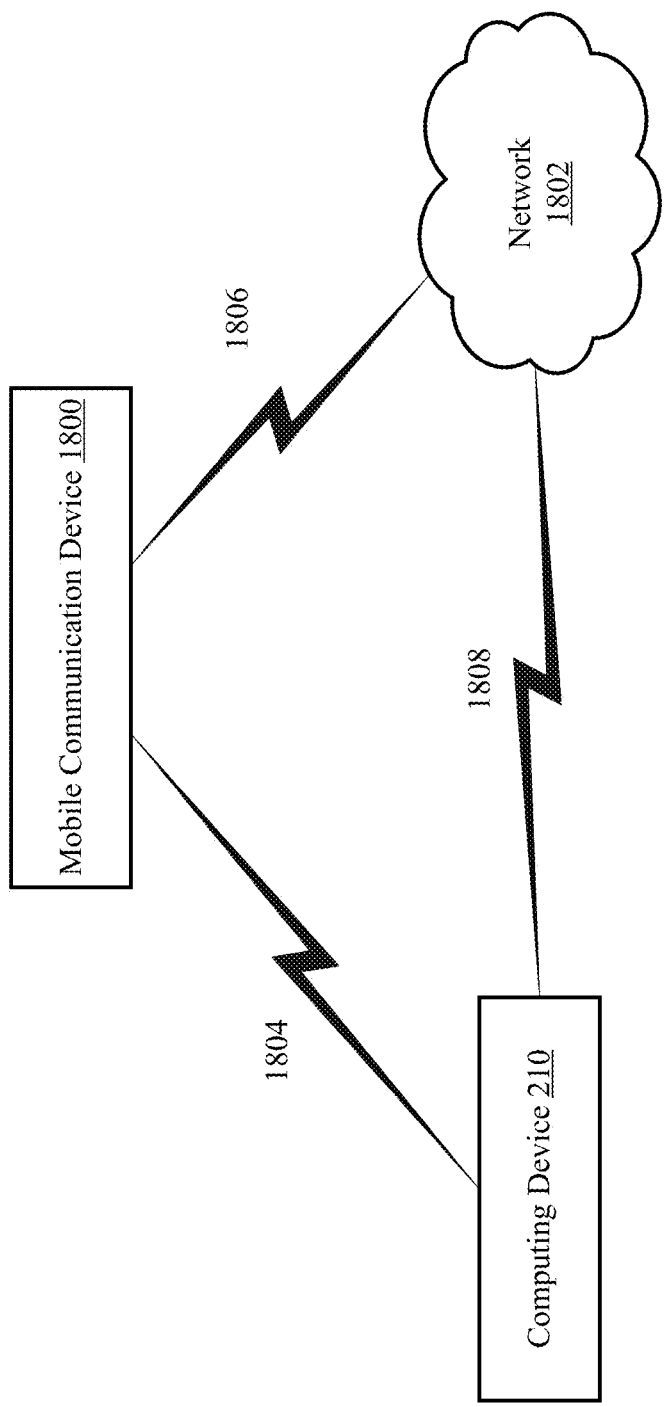
FIG. 18 provides an illustration of an illustrative system for controlling operations of a cart.

As shown in FIG. 17, the computing device 210 comprises a user interface 1702, a Central Processing Unit ("CPU") 1706, a system bus 1710, a memory 1712 connected to and accessible by other portions of computing device 210 through system bus 1710, a system interface 1762, and hardware entities 1714 connected to system bus 1710. The user interface can include input devices and output devices, which facilitate user-software interactions for controlling operations of the computing device 210. The input devices include, but are not limited to, a physical and/or touch keyboard 1750. The input devices can be connected to the computing device 210 via a wired or wireless connection (e.g., a Bluetooth® connection). The output devices include, but are not limited to, a speaker 1752, a display 1754, and/or Light Emitting Diodes ("LEDs") 1756. The touch screen display 150 may comprise display 1754 or be separate from display 1754. System interface 460 is configured to facilitate wired or wireless communications to and from external devices. The external devices can include, but are not limited to, network nodes (such as access points), and/or mobile communication devices (e.g., a smart phone). An individual may control operations of the cart 100 via a mobile communication device 1800 of FIG. 18 that is communicatively coupled directly to the computing device 210 via a Short Range Communications ("SRC") link 1804 and/or Long Range Communications ("LRC") links 1806, 1808 through a network 1802 (e.g., the Internet, an Intranet, and/or a cellular network).

At least some of the hardware entities 1714 perform actions involving access to and use of memory 1712, which can be a Random Access Memory ("RAM"), a disk drive, flash memory, a Compact Disc Read Only Memory ("CD-ROM") and/or another hardware device that is capable of storing instructions and data. Hardware entities 1714 can include a disk drive unit 1716 comprising a computer-readable storage medium 1718 on which is stored one or more sets of instructions 1720 (e.g., software code) configured to implement one or more of the methodologies, procedures, or functions described herein. The instructions 1720 can also reside, completely or at least partially, within the memory 1712 and/or within the CPU 1706 during execution thereof by the computing device 210. The memory 1712 and the CPU 1706 also can constitute machine-readable media. The term "machine-readable media", as used here, refers to a single medium or multiple media (e.g., a centralized or distributed database, and/or associated caches and servers) that store the one or more sets of instructions 1720. The term "machine-readable media", as used here, also refers to any medium that is capable of storing, encoding or carrying a set of instructions 1720 for execution by the computing device 210 and that cause the computing device 210 to perform any one or more of the methodologies of the present disclosure.

The computing device 210 also comprises a clock/timer 1760 and a selective power connect mechanism 1764. The clock/timer 1760 is configured to track an amount of time that a clean process has been performed. In this regard, it should be understood that the clock/timer 1760 is set to zero when a new iteration of a clean process is started. The CPU 1706 uses time information from the clock/timer 1760 to determine when a clean process should be terminated or discontinued. For example, when the time information indicates that a threshold period of time (e.g., 5 minutes or 240 minutes) has expired, the CPU 1706 determines that the clean process should be terminated or discontinued. As such, the CPU 1706 causes the cart 100 to transition from a clean mode in which the UV lamp(s) is(are) activated to a standby mode in which the UV lamps are deactivated. In response to the mode change, the selective power connect mechanism 1764 is operated to cause power to no longer be supplied to the UV lamp ballast component 208 and/or UV lamps 500. The present solution is not limited to the particulars of this example. The selective power connect mechanism 1764 may include, but is not limited to, a relay, a transistor, or switch.

Referring again to FIG. 2, a plurality of shelves 250 are disposed within the main chamber 228 of the cart 100. The shelves 250 are configured to structurally support the electronic devices 220, trays and/or other shelf components when disposed in the cart 100. Each shelf 250 is sized and shaped to receive an electronic device in a closed position and/or an opened position. The total number of shelves 250 is selected in accordance with a given application. For example, if the cart 100 is designed to receive a maximum of 10 electronic devices in the main chamber 228, then 10 shelves 250 are provided. The present solution is not limited to the particulars of this example.

The shelves 250 are designed to be removed from the cart 100 and re-inserted into the cart 100. Illustrations of an illustrative architecture for the shelves 250 are provided in FIGS. 8-12. As shown in FIGS. 8-12, the shelf 250 comprises a wire shelf 800 to which couplers 900, 902 are fixedly attached. The couplers 900, 902 provide a means to structurally and mechanically couple the wire shelf 800 to tracks 1200, 1202 disposed within the main chamber 228 of the cart. In this way, the shelves' relative positions within the cart can be adjusted, and/or the total number of shelves disposed within the cart can be modified for any given application. The present solution is not limited to the shelf/track architecture shown in FIGS. 8-12. In other scenarios, at least one shelf comprises a planar transparent shelf or a planar highly reflective coated shelf. For example, the at least one shelf is formed of plastic, acrylic, glass, and/or any other material that allows UV light to pass therethrough in an amount sufficient to disinfect all or a portion of a surface of an electronic device. Additionally or alternatively, the shelves are securely coupled to the tracks, but are able to be pulled out of the cart and pushed into the cart.

One or more couplers 904, 908 may be fixedly or removably coupled to each shelf 500. Each coupler 904 is configured to facilitate cable management within the main chamber 228 of the cart 100. In this regard, each coupler 904 has an insert space 906 into which the cable 224 can be inserted, compressed, and/or fictionally engaged. The coupler 904 ensures that the cable 224 is held in position relative to a shelf 500 while the cable is coupled to an electronic device 220 disposed within the cart 100. Known or to be known couplers can be used here for cable management. Each coupler 908 is configured to provide a secondary locking mechanism for a door 106, 108. When the door is closed, the coupler 908 is mechanically or magnetically coupled to the rear of the door, and thus helps to maintain the door is its closed position even when the primary door latch 130, 132 is not operating properly or an individual fails to latch the door properly. Known or to be known couplers can be used here for maintaining the door in the closed position. For example, in the mechanical coupling scenario, the coupler may be designed to mate with another coupler disposed on the rear of the door, and/or engage a protruding structure disposed on the rear of the door (e.g., the coupler has an insert space into which the protruding structure can received, compressed, snappingly, latchingly, and/or frictionally engaged). In the magnetic scenarios, the magnet would be configured to magnetically attract the door either formed of a metal or coated with a metal. The present solution is not limited to the particulars of these examples. The coupler 904 and 908 can be the same as each other or different than each other. The couplers 904, 908 can include, but are not limited to, mechanical clips (as shown), mechanical clamps, latches, and/or magnets.

Figure 19A:
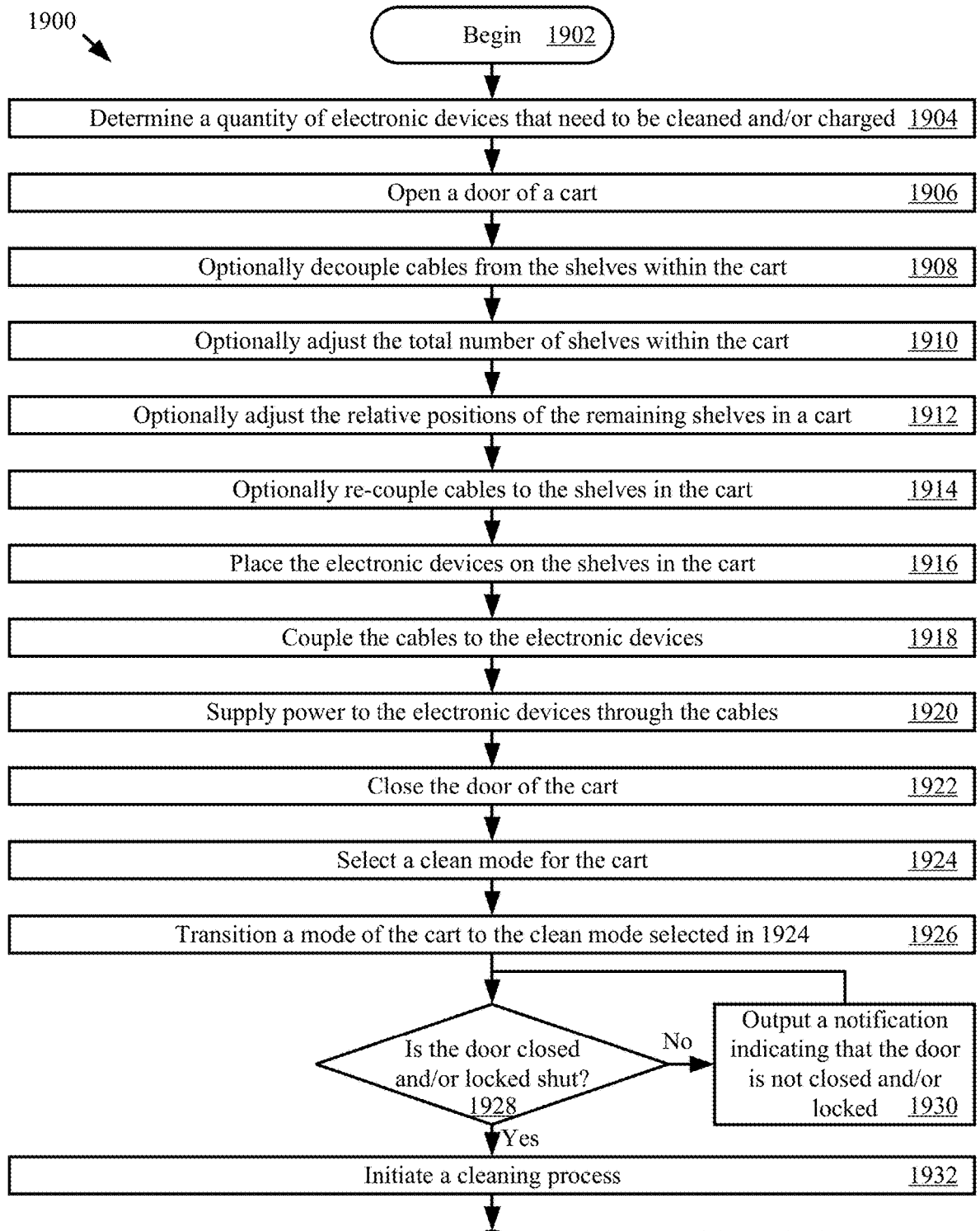
FIGS. 19A-19B (collectively referred to as "FIG. 19") provide a flow diagram of an illustrative method for operating a cart.
Figure 19B:
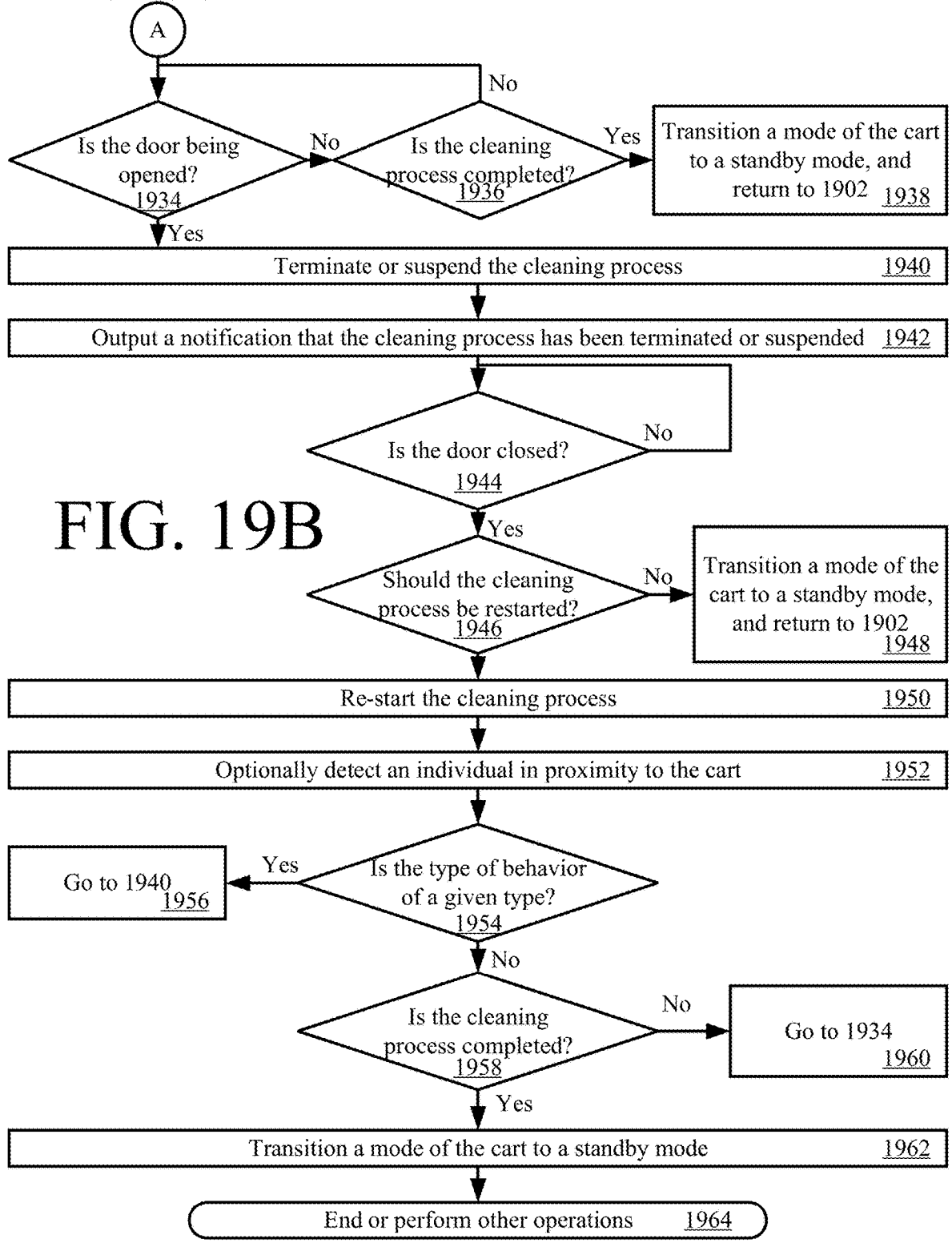

Referring now to FIG. 19, there is provided a flow diagram of an illustrative method 1900 for operating a cart (e.g., cart 100 of FIGS. 1-7). Method 1900 begins at 1902 and continues to 1904 where a determination is made as to a quantity of electronic devices that need to be cleaned and/or charged by the cart. Next in 1904, a door (e.g., door 108 of FIGS. 1-7) is opened by an individual (e.g., by actuating a door latch 132 of FIGS. 1-7, and pulling the door out and away from the cart's housing 102 of FIGS. 1-7 such that the door rotates 270° about a pin 1400 of at least one hinge 1300 of FIGS. 13-14). In optional 1908-1914, the following actions are taken by the individual: decouple cables (e.g., cables 224 of FIG. 2) from the shelves (e.g., shelves 250 of FIG. 2) within the cart; adjust the total number of shelves within the cart; adjust the relative positions of the remaining shelves in the cart; and/or re-couple the cables (e.g., cables 224 of FIG. 2) to the remaining shelves in the cart.

In 1916, the electronic devices (e.g., electronic devices 220 of FIG. 2) are placed on the shelves in the cart by the individual. Notably, the shelves are sized and shaped so that the electronic devices may be placed therein in their opened positions. For example, a laptop computer is able to transition between a closed position and an opened position, as known in the art. The laptop computer can be transitioned to its opened position prior to being placed on a shelf of the cart. The present solution is not limited to the particulars of this example.

In 1918, the cables (e.g., cables 224 of FIG. 2) are coupled to the electronic devices disposed within the cart. The cables facilitate the supply of power to the electronic devices and/or the charging of power sources of the electronic devices (e.g., rechargeable batteries). Accordingly, power is supplied to the electronic devices in 1920 via the cables. The power may be constantly supplied to the electronic devices while a power supply component 206 is connected to an external power source (e.g., an AC mains).

In 1922, the door of the cart is closed by the individual (e.g., by causing the door to rotate 270° about a pin 1400 of at least one hinge 1300 of FIGS. 13-14, and actuating a door latch 132 of FIGS. 1-7 to lock the door in its closed position). The individual then performs actions in 1924 to select a clean mode for the cart. The clean mode can be selected by interacting with a touch screen display (e.g., touch screen display 150 of FIGS. 1-7) of the cart to perform a user-software interaction for selecting a mode from a plurality of modes. Alternatively, the clean mode is selected by performing a user-software interaction with a mobile communication device (e.g., mobile communication device 1800 of FIG. 1) in the individual's possession. The mobile communication device sends a mode selection signal to the cart in response to the user-software interaction. In response to the clean mode selection, the cart performs operations in 1926 to transition from a standby mode in which the UV lamps are deactivated to the clean mode.

In the clean mode, a computing device (e.g., computing device 210 of FIG. 2) performs operations to determine if the door(s) of the cart is(are) closed and/or locked shut. In some scenarios, the computing device makes this determination based on data generated by one or more sensors 230 of the cart (e.g., magnetic door sensor(s)). If the door(s) is(are) not closed and/or locked shut [1928:NO], then 1930 is performed where the cart outputs a notification indicating that the door is not closed and/or locked. This notification can include, but is not limited to, a visual notification (e.g., light emitted from an LED 1756 of FIG. 17, and/or content displayed on the cart's display (e.g., touch screen display 150 of FIGS. 1-7) and/or a mobile communication device's display), an auditory notification (e.g., sound or speech output from speaker 1752 of FIG. 17), and/or a tactile notification (e.g., vibration(s) generated by a vibration generator of the computing device 210 of FIG. 2 and/or mobile computing device 1800 of FIG. 18). Method 1900 then returns to 1928 to once again determine if the door(s) is(are) closed and/or locked shut.

If the door(s) is(are) not closed and/or locked shut [1928: YES], then 1932 is performed where a cleaning process of the cart is initiated. UV lamp(s) (e.g., UV lamps 500 of FIG. 5) of the cart are enabled or otherwise turned on when the cleaning process is initiated. The UV lamp(s) remain on throughout the cleaning process such that the external surfaces of the electronic device(s) disposed in the cart are sanitized by the same. Method 1900 then continues with 1934 of FIG. 19B. The cart continuously monitors the door position(s) through the cleaning process. As such, 1934 involves determining whether a door of the cart is being opened. If a cart door is being opened [1934:NO], then 1936 is performed where a determination is made by the computing device of the cart as to whether the cleaning process has been completed (e.g., based on an expiration of given period of times such as 5 minutes or 240 minutes). If the cleaning process has not been completed [1936:NO], then method 1900 returns to 1934. If the cleaning process has been completed [1936:YES], then 1938 is performed where the mode of the cart is transitioned back to the standby mode. Method 1900 then returns to 1902.

If the door(s) is(are) being opened [1934:YES], then 1940 is performed where the cleaning process is terminated or suspended. The UV lamp(s) of the cart are disabled or otherwise turned off when the cleaning process is terminated or suspended. A clock/timer (e.g., timer 1760 of FIG. 17) of the cart is also stopped when the cleaning process is terminated or suspended. A notification is output in 1842 from the cart and/or the mobile communication device. The notification indicates that the cleaning process has been terminated or suspended. The notification may also specify a reason why the cleaning process was terminated or suspended (e.g., a door is open).

In 1944, the computing device of the cart determines whether the door is closed once again. If the door is not closed [1944:NO], then method 1900 returns to 1944. If the door is closed [1944:YES], then 1946 is performed where the cart's computing device determines if the cleaning process should be restarted. This determination may be made based on a user-software interaction with the cart. If the cleaning process should not be restarted [1946:NO], then a mode of the cart is transitioned to the standby mode as shown by 1948. Method 1900 may also return to 1902. If the cleaning process should be restarted [1946:YES], then the cart's computing device performs operations in 1950 to restart the cleaning process, for example, by enabling or otherwise turning on the UV lamps once again and re-starting a timer (e.g., timer 1760 of FIG. 17).

It should be noted that the cart may employ machine learning technology to learn behaviors of individual's in proximity to and/or interacting with the cart, and to control operations based on the learned behaviors. Accordingly, method 1900 may include optional operations 1952-1962 directed to machine learning algorithms implemented by the computing device of the cart. In some scenarios, the machine-learning algorithm includes, but is not limited to, a decision tree learning algorithm, an association rule learning algorithm, an artificial neural network learning algorithm, a deep learning algorithm, an inductive logic programming based algorithm, a support vector machine based algorithm, a clustering based algorithm, a Bayesian network based algorithm, a representation learning algorithm, a similarity and metric learning algorithm, a sparse dictionary learning algorithm, a genetic algorithm, a rule-based machine learning algorithm, and/or a learning classifier systems based algorithm. Each of these listed types of machine-learning algorithms is well known in the art. The machine-learning process implemented by the present solution can be built using Commercial-Off-The-Shelf ("COTS") tools (e.g., SAS available from SAS Institute Inc. of Cary, North Carolina).

Operation 1952 involves detecting an individual in proximity to the cart (e.g., within 5-15 feet of the cart). This detection can be made based on data generated by sensor(s) of the cart (e.g., a proximity sensor such as a beam break sensor) and/or SRCs (e.g., Bluetooth or WiFi communications) between the cart and the mobile communication device. When an individual is detected in 1952, the cart's sensor(s) collect(s) information about the individual's behavior. For example, sensor data is generated at the cart that specifies the location of the individual relative to the cart, a direction in which the individual is traveling, a speed at which the individual is traveling, whether the individual is carrying an object, a type of the object (e.g., an electronic device), gestures being made by the individual, and/or an estimated amount of time until the individual reaches the cart. This sensor data is processed and/or compared to pre-stored behavior patterns to determine or predict a type of behavior being performed by the detected individual. For example, the individual's behavior is determined to be of a door opening type when (s)he is walking towards the cart, stops N feet away from the cart, and/or is carrying an electronic device (e.g., a portable computer). The present solution is not limited to the particulars of this example. If the type of behavior is of a given type or is predicted to be of a given type (e.g., a door opening type, an electronic device insertion type, and/or an electronic device removal type) [1954:YES], then 1956 is performed where method 1900 continues to 1940. If the type of behavior is not of a given type or is not predicted to be of a given type [1954: NO], then the cart's computing device determines if the cleaning process is completed. This determination can be made based on whether a given amount of time has passed since the cleaning process was initiated. If not [1958:NO], then 1960 is performed where method 1900 continues with

1934. If so [1958:YES], then a mode of the cart is transitioned to the standby mode as shown by 1962. Subsequently, 1964 is performed where method 1900 ends or other operations are performed (e.g., return to 1902 of FIG. 19A).

Although the present solution has been illustrated and described with respect to one or more implementations, equivalent alterations and modifications will occur to others skilled in the art upon the reading and understanding of this specification and the annexed drawings. In addition, while a particular feature of the present solution may have been disclosed with respect to only one of several implementations, such feature may be combined with one or more other features of the other implementations as may be desired and advantageous for any given or particular application. Thus, the breadth and scope of the present solution should not be limited by any of the above described embodiments. Rather, the scope of the present solution should be defined in accordance with the following claims and their equivalents.

What is claimed is:

1. A method for operating a cart, comprising:
   receiving at least one electronic device on a shelf of a plurality of shelves disposed in a main chamber of the cart, the at least one electronic device being in an open position and the shelf being configured to allow UV light to pass therethrough to a surface of the at least one electronic device;
   supplying power from the cart to the at least one electronic device;
   transitioning a mode of the cart from a first mode in which at least one UV lamp is disabled to a second mode during which at least one UV lamp is to be enabled;
   detecting, by a computing device, that at least one door of the cart is in a closed position;
   causing, by the computing device, an enablement of the at least one UV lamp that is disposed in the main chamber of the cart, responsive to a detection that the at least one door is in the closed position;
   using light from the at least one UV lamp to clean the surface of the at least one electronic device while power is being supplied from the cart to the at least one electronic device;
   using at least one first sensor of the cart to detect when an individual comes in proximity to the cart while the surface of the at least one electronic device is being cleaned via the at least one UV lamp;
   responsive to said detecting, enabling at least one second sensor to generate sensor data prior to the individual coming in contact with the cart, the sensor data indicating at least one of a location of the individual relative to the cart, a direction of travel for the individual, a traveling speed for the individual, a type of an object being carried by the individual, and a body movement being made by the individual;
   processing the sensor data to predict or determine a type of a behavior of the individual using a machine learning algorithm that is trained to detect patterns in human behavior; and
   disabling the at least one UV lamp when the type of behavior of the individual is predicted or determined to be of a given type, or continuing using light from the at least one UV light to clean the at least one electronic device when the type of behavior of the individual is predicted or determined to not be of the given type.

2. The method according to claim 1, wherein the shelf comprises a wire shelf or a shelf formed of a transparent material.

3. The method according to claim 1, further comprising detachably coupling at least one cable to the shelf, the cable facilitating a supply of power from the cart to the at least one electronic device.

4. The method according to claim 1, further comprising detachably coupling the at least one door to the shelf when the at least one door is in the closed position.

5. The method according to claim 1, further comprising:
   detecting that the at least one door is being opened while the surface of the at least one electronic device is being cleaned via the at least one UV lamp; and
   disabling the at least one UV lamp responsive to a detection that the at least one door is being opened.

6. The method according to claim 5, further comprising:
   detecting when the at least one door is once again in the closed position; and
   enabling the at least one UV lamp responsive to a detection that the at least one door is once again in the closed position.

7. The method according to claim 1, further comprising transitioning the mode of the cart from the second mode back to the first mode upon completion of a cleaning process in which the UV lamp is used to clean the surface of the at least one electronic device.

8. The method according to claim 1, further comprising disabling the at least one UV lamp upon expiration of a given period of time.

9. The method according to claim 8, further comprising transitioning the mode of the cart back to the first mode when the at least one UV lamp is disabled.

* * * * *